United States Patent [19]

Soós et al.

[11] 4,450,309

[45] May 22, 1984

[54] PROCESS FOR THE PREPARATION OF UNSATURATED GEMINAL DIHALOGEN COMPOUNDS

[75] Inventors: Rudolf Soós; József Nemes; László Vidra,

[73] Assignee: Chinoin Gyogyszer es Vegyeszeti Termekek Gyar Rt., Budapest, Hungary

[21] Appl. No.: 391,866

[22] Filed: Jun. 24, 1982

[30] Foreign Application Priority Data

Jul. 3, 1981 [HU] Hungary .............................. 1945/81

[51] Int. Cl.$^3$ .............................................. C07C 17/33
[52] U.S. Cl. ..................................... 570/217; 570/218
[58] Field of Search .................................. 570/217, 218

[56] References Cited

FOREIGN PATENT DOCUMENTS 16505 10/1980 European Pat. Off. ............. 570/217

OTHER PUBLICATIONS

"Relation between Chemical Structure and Insecticidal Activity in Pyrethroid Compounds, I" Collection Czechoslov. Chem. Commun., vol. 24 (1959), pp. 2230–2236.

Primary Examiner—Charles F. Warren
Assistant Examiner—Joseph A. Boska
Attorney, Agent, or Firm—Karl F. Ross; Herbert Dubno

[57] ABSTRACT

The invention relates to a new process for preparing unsaturated geminal dihalogen compounds. More particularly, the invention concerns a process for preparing compounds of the formula (I) t,0010 wherein

X is halogen, $R^1$ is a straight or branched chained alkenyl group having 2 to 6 carbon atoms, by clearing the corresponding 1-substituted 2,2,2-trihaloethylesters.

7 Claims, No Drawings

PROCESS FOR THE PREPARATION OF UNSATURATED GEMINAL DIHALOGEN COMPOUNDS

The invention relates to a new process for the preparation of unsaturated geminal dihalogen compounds. More particularly, the invention concerns the preparation of compounds of the formula (I)

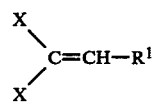

wherein
X is halogen,
$R^1$ is a straight or branched chained alkenyl group having 2 to 6 carbon atoms.

According to the invention the compounds of formula (I) are prepared by clearing 1-substituted 2,2,2-trihaloethylesters.

The 2,2,2-trichloroethoxy group has been used for protecting carboxylic acids since 1966 [J.Am.Chem. Soc. 88, 852 (1966); J.Org.Chem. 34, 3552 (1969) and J. Am.Chem.Soc. 94, 1022 (1972)].

The trichloroethoxycarbonyl group is widely used for protecting hydroxyl and amino functional groups [Tetrahedron Letters 2555 (1967): J.Am.Chem.Soc. 94, 1411 (1972) and Can.J.Chem. 47 2906 (1969)].

Due to their specific character these protecting groups can easily be removed by metallic Zn in acetic acid or hot alcohol.

The references cited above clearly illustrate that the 2,2,2-trichloroethoxy group has particularly been used in the synthesis of cephalosporins and other sensitive molecules. Their elimination was carried out with 3 to 15 equivalents of zinc [Chemické Listy, 52, 688–694 (1958)] and smaller amounts of the desired end product could be produced by a relatively well controlled process with a good yield. If higher amounts are to be produced, the handling of the large amounts of zinc pose a problem and the reaction is very difficult to control. Frequently the reaction is initiated after a certain induction period whereupon it is suddenly speeded up due to the exothermic character of the reaction and, as a result, the reaction mixture often foams out of the reaction vessel. These disadvantages take place in particular when less than 3 to 5 mol.-equivalents of zinc are employed.

The induction period and a subsequent sudden increase of the reaction speed are often observed during the reductive splitting of 2,2,2-trichloroethyl esters (e.g. if in the formula (II) R stands for methyl, $R^1$ is 2,2-dimethylvinyl) when a mixture of zinc, ether and glacial acetic acid or zinc and methanol is employed. Cooling is not suitable for controlling the reaction since it may result in termination of the reaction.

It has now, surprisingly, been found that if a 0.01 to 1.5 molar equivalent amount of an inorganic acid is simultaneously added, the reaction takes place instantly, with a total conversion. Moreover, there is no need for boiling the solvent, since the reaction proceeds even at 0° C. smoothly and about 1 mol.-equivalent of a suitable metal, e.g. zinc is entirely sufficient to obtain the desired result.

If a 1-substituted 2,2,2-trichloroethyl ester starting material and an inorganic acid are simultaneously added, the total amount of an ester added subsequently into the zinc suspension, is reacted instantaneously. The reaction velocity can be controlled by adjusting the rate of addition as desired. If desired, the reaction mixture may also be cooled since the reaction proceeds even at 0° C. rapidly. The process according to the invention can be carried out also continuously.

The process according to the invention has an electrochemical explanation. Semmelhack and Heinsohn carried out experiments as to the elimination of various protecting groups, e.g. 2,2,2-trichloroethoxy group by electrolysis with a controlled potential [J.Am.Chem.-Soc. 94, 5139 (1972)]. They established that if the electrolysis was carried out using Hg as a working electrode and calomel as a reference electrode, with a voltage of −1.65, the reduction of 2,2,2-trichloroethyl benzoate could be illustrated by the following reaction equation:

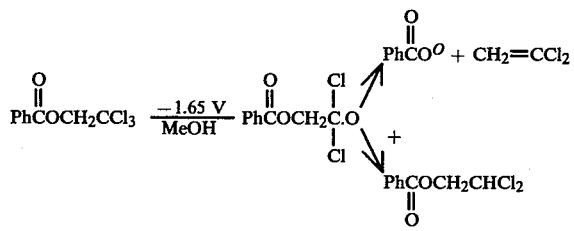

As a first step an anion is formed on the working electrode by the reduction of a halogen, which is stabilized by concerted elimination as a result of the formation of 1,1-dichloroethylene and a benzoate anion. In addition, in a simultaneous reaction 6% of a dichloroethyl benzoate by-product is obtained due to the protonation of the anion. The ratio of the by-product to the main product is essentially a function of the leaving group.

A good leaving group and an antiperiplanaric position of the negative charge and the leaving group favor the reductive elimination [Zh. Obshch. Khim. 43, 515 (1973)].

The reaction disclosed in the present application is an electroreduction as well. The presence of a 0.01 to 1.5 mol.-equivalent amount of an acid leads to the formation of a local cell, in which, due to an overvoltage of hydrogen, instead of hydrogen evolution the Cl-substituted 2,2,2-trichloroethyl group is reduced. When reducing a 1-substituted-2,2,2-trichloroethyl or trichloroethoxycarbonyl group by a zinc/glacial acetic acid or zinc/alcohol system, it is presumed that the reaction proceeds through zinc-haloalkyl complexes (so called "Reformatzkij intermediate") whereupon the elimination takes place through the electron pair between the carbon and zinc, which is strongly polarized in the direction of carbon. By this mechanism it can be reasonably explained why the presence of 2,2-dichloroethyl esters could not be detected in the product [see e.g. J.Am.Chem.Soc. 94, 5140, 2nd paragraph (1972)]. On the other hand, if 1,1,1-trichloro-2-acetoxy-4-methoyl-pentene is reduced by the process according to the invention, the presence of 1,1-dichloro-2-acetoxy-4-methyl-pentene can be detected, which proves that the reaction is an electroreduction, more particularly, a chemical electroreduction.

Though according to the invention 0.01 to 1.5 mol.-equivalents of a strong inorganic acid are added to the reaction mixture, the pH remains practically neutral.

This is essential, since if acid-sensitive molecules, e.g. 1,1-dichloro-4-methyl-1,3-pentadiene are to be reduced, the reaction can be accomplished only under neutral or slightly acidic conditions, just as in the case when acetic acid or an alcohol is used as a reaction medium. In the same time, according to the invention the reliability of the reaction is incomparably better, the reaction is easier to control and excellent yields can be achieved.

In the case of benzoyloxy or alkanoyloxy groups, which are considered better leaving groups, the ratio of the protonated 2,2-dichloroalkyloxy by-product is considerably lower.

According to the invention a compound of the formula (II)

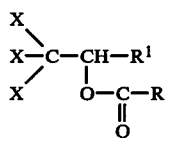

in which

X and $R^1$ are as hereinbefore defined, and

R is hydrogen, a straight or branched chained alkyl group having 1 to 6 carbon atoms or an optionally substituted aryl or aralkyl group, is reacted with 1 to 2 mol-equivalents of zinc, aluminum, tin, iron or magnesium and 0.01 to 1.5 mol-equivalents of a mineral acid and/or an acidic salt thereof, in a water-miscible organic solvent, at a temperature between 0° C. and 200° C.

The process is carried out preferably by adding a solution of the compound of the formula (II) in a water-miscible organic solvent and an aqueous solution of a mineral acid simultaneously to a suspension of 1 to 2 mol. equivalents of zinc, aluminum, iron or magnesium powder in an organic solvent.

Preferably a solution of the compound of the formula (II) in a water-miscible organic solvent and an aqueous solution of a mineral acid are simultaneously added to a suspension of 1 to 2 mol. equivalents of zinc, aluminum, iron or magnesium powder in an organic solvent.

More particularly a solution of the compound of the formula (II) and 0.01 to 0.1 mol. equivalents of a mineral acid and/or an acidic salt thereof is a water-miscible organic solvent to a suspension of 1 to 2 mol. equivalents of zinc, aluminum, iron or magnesium powder in a water-miscible organic solvent is provided.

Examples of the water-miscible organic solvent include alkanols having 1 to 4 carbon atoms such as methanol or ethanol, cyclic or linear ethers preferably tetrahydrofuran or dimethoxyethane, oxo compounds such as dimethyl formamide, acetone, carboxylic acids having 1 to 4 carbon atoms, preferably acetic acid, or carboxylic acid anhydrides having 3 to 6 carbon atoms, preferably acetic anhydride.

Preferably the reaction between the compound of the formula (II) and the zinc, aluminum, iron or magnesium powder is carried out at the boiling temperature of the mixture of the organic solvent and water.

Preferably the mineral acids employed in the process are hydrochloric acid, sulfuric acid, phosphoric acid or perchloric acid.

Preferably the acid salts employed in the process are alkali hydrosulfate, alkali hydrogen phosphate or alkali dihydrogen phosphate.

According to a preferred embodiment of the reaction to a suspension of the zinc powder in a water-miscible organic solvent a 1-substituted-2,2,2-trichloroethyl ester and an aqueous solution of the mineral acid are simultaneously added. Thus, the reaction velocity can conveniently be controlled by the rate of the addition.

At a temperature between 0° C. and the boiling point of the reaction mixture the reaction takes place instantenously, and in this way the reductive elimination can be carried out under substantially milder conditions than by any of the methods known in the art. The process according to the invention has no great demands as to the purity of the starting material. Crude products obtained by acylation and starting materials purified by distillation can equally be used. For example, 1-substituted-2,2,2-trichloroethanol compounds can be converted into the corresponding acetyl derivatives by acetic anhydride, for example in the presence of sulfuric acid as a catalyst in a known manner, and the reaction mixture obtained can directly be added to the methanolic suspension of zinc powder, simultaneously with a given amount of an inorganic acid. During the acylation there are anhydrous conditions in the reaction mixture, consequently, the redox potentials are not the same as in an aqueous medium. The 5 to 10 mol.-% sulfuric acid catalyst catalyzes the chemical electroreduction according to the mechanism described hereinbefore. Due to the anhydrous conditions 5 to 10 mol-% of sulfuric acid are sufficient to ensure an instantaneous reaction.

According to a more preferred embodiment of the invention an acylation mixture containing 5 to 10 mol.-% of sulfuric acid is added to an alcoholic suspension of magnesium, iron or preferably zinc. The method can preferably be used to prepare intermediates for the synthesis of pyrethroids.

Further details of the invention are to be found in the following Examples which are not intended to limit our invention in any way.

EXAMPLE 1

16 g. (245 mmoles) of zinc powder are suspended in 200 ml. of methanol, whereupon a solution of 50 g. (0.203 moles) of 1,1,1-trichloro-2-acetoxy-4-methyl-3-pentene in 50 ml. of methanol and 101.5 ml. (0.203 moles) of a 2 molar aqueous sodium hydrogensulfate solution are simultaneously added in 20 minutes, on an outer water bath of 10° to 15° C. By the regulation of the rate of addition the temperature of the reaction mixture may be kept under 40° C.

When the addition is complete, 0.1 g. of butylhydroxytoluene are added to the reaction mixture, whereupon the precipitated salts and other solids are filtered off by a G-2 glass filter. The salt filtered off is slurried in 50 ml. of methanol and subsequently in two 50-ml. portions of methylene chloride and is then filtered by suction. The filtrates are combined, the combined bi-phase system is diluted with 1 lit. of water and the lower organic phase is separated. The aqueous phase is extracted with three 50-ml. portions of methylene chloride, the organic phases are combined, dried over sodium sulfate and filtered. The organic solvents are distilled off under normal pressure, using a 50-cm. Vigreux column. The residue is fractionated under a pressure of 25 to 35 mmHg. As a main product a fraction distilled between 90° C. and 100° C. is collected. After distillation 28.6 g. (93.2%) of 1,1-dichloro-4-methyl-1,3-pentadiene are obtained.

t.l.c. analysis: $R_f$=0.6 on a Silicagel G plate (Merck, Art. No. 5719) in hexane. The product can be detected by u.v. illumination.

NMR (CDCl$_3$, δ): 5.98 (ddq, 1H, C$\underline{H}$=C/CH$_3$/$_2$); 6.62 (d,1H,C$\underline{H}$=CCl$_2$); 1.88 and 1.8 (d+d, 3H+3H, =C(CH$_3$)$_2$).

From an aliquot sample 5.5% of 1,1-dichloro-2-acetoxy-4-methyl-3-pentene by-product can be isolated related to the starting compound. The isolation is performed by column chromatography carried out on a silicagel column, using a 1:1 mixture of benzene and hexane as an eluent. After the elution the fractions corresponding to R$_f$=0.19 on a Silicagel G plate are collected and evaporated.

According to t.l.c. analysis of the by-product carried out on a Merck Silicagel G plate (Art. No. 5719), using a 1:1 mixture of hexane and benzene for the development R$_f$=0.19. The detection is performed with a 10% phosphomolybdenic acid solution.

NMR (CDCl$_3$,): 5.8 (q,1H,CHOAc); 5.75 (d,1H,CHCl$_2$); 5.27 (dq,1H,CH=$\overline{C}$(CH$_3$)$_2$); 2.1 (s,3H,C$\overline{O}$CH$_3$); 1.8 (s,6H,=C(CH$_3$)$_2$).

EXAMPLE 2

26.6 g. (407 mmoles) of zinc powder are suspended in 250 ml. of methanol whereupon 50 g. (0.203 moles) of 1,1,1-trichloro-2-acetoxy-4-methyl-3-pentene are added. The suspension is cooled to 10° C. on an ice-water bath, whereupon a solution of 101.5 ml. (0.203 moles) of a 2 M aqueous sodium hydrogensulfate solution cooled up to 0° C. are added. Following the addition the reaction mixture is treated as described in Example 1. 24.3 g. (82.2%) of distilled 1,1-dichloro-4-methyl-1,3-pentadiene are obtained. The analytical characteristics of the product are identical with those of the product of Example 1.

In an amount of 8 to 10% related to the starting material a 1,1-dichloro-2-acetoxy-4-methyl-3-pentene by-product can also be detected.

EXAMPLE 3

Following the procedure of Example 1 but replacing 1,1,1-trichloro-2-acetoxy-4-methyl-3-pentene by 1,1,1-trichloro-2-ethylcarbonyloxy-4-methyl-3-pentene, 29.2 g. (95.3%) of 1,1-dichloro-4-methyl-1,3-pentadiene are obtained. As a by-product 2.6% of 1,1-dichloro-2-ethylcarbonyloxy-4-methyl-3-pentene are obtained.

EXAMPLE 4

Following the procedure of Example 1 but replacing 1,1,1-trichloro-2-acetoxy-4-methyl-3-pentene by 1,1,1-trichloro-2-acetoxy-4-methyl-4-pentene, 28.4 g. (92.6%) of 1,1-dichloro-4-methyl-1,4-pentadiene are obtained, boiling at 40° to 60° C. (10–15 mmHg).

NMR (CDCl$_3$): /5.9/ t,1H, CHCCl$_2$/; 4.8 (s, 2H, C=CH$_2$); 2.9 (d, Cl$_2$CCHCH$_2$); 1.77 (s, 3H, CH$_3$).

In addition to the main product 6% of 1,1-dichloro-2-acetoxy-4-methyl-4-pentene are obtained.

Analysis results: According to t.l.c. carried out on a Silicagel G plate (Merck, Art. No. 5719) R$_f$=0.65 (in benzene) or 0.375 (in a 1:1 mixture of benzene and hexane). The development is performed with a 10% phosphomolybdenic acid.

EXAMPLE 5

Following the procedure described in Example 1 but replacing 16 g. of zinc powder by 26.6 g. (406 mmoles) of zinc powder 28.8 g. (93.8%) of distilled 1,1-dichloro-4-methyl-1,3-pentadiene are obtained. The analytical characteristics of the product are identical with those given in Example 1.

EXAMPLE 6

The procedure described in Example 1 is followed except that instead of a sodium hydrogensulfate solution 101.5 ml. of a 2 M aqueous hydrochloric acid solution are added. In this case filtration can be omitted when working the product since the zinc salt formed remains dissolved in the aqueous solution. Thus 28 g. (91.2%) of 1,1-dichloro-4-methyl-1,3-pentadiene are obtained. The characteristics of the product are identical with those of the product of Example 1. In the process about 7% of a by-product is formed.

EXAMPLE 7

The procedure described in Example 1 is followed except that instead of sodium hydrogensulfate 101.5 ml. of a 1 M aqueous sulfuric acid solution are added. Thus 27.3 g. (89.1%) of distilled 1,1-dichloro-4-methyl-1,3-pentadiene are formed. The analytical characteristics of the product are identical with those of the product of Example 1. The 1,1-dichloro-2-acetoxy-4-methyl-3-pentene by-product is formed in an amount of 9% relative to the starting compound.

EXAMPLE 8

The procedure described in Example 1 is followed except that 1,1,1-trichloro-2-acetoxy-4-methyl-3-pentene is replaced by 1,1,1-trichloro-2-formyloxy-4-methyl-3-pentene. 24.8 g. (81%) of 1,1-dichloro-4-methyl-1,3-pentadiene are obtained. The analytical characteristics of the distilled product are identical with those of the product of Example 1.

EXAMPLE 9

The procedure described in Example 1 is followed except that 1,1,1-trichloro-2-acetoxy-4-methyl-3-pentene is replaced by 62.5 g. of 1,1,1-trichloro 2-benzoyloxy-4-methyl-3-pentene. 28.7 g. (93.8%) of distilled 1,1-dichloro-4-methyl-1,3-pentadiene are obtained. The analytical characteristics of the product are identical with those of the product of Example 1.

In addition to the main product 1.95 g. (3.5%) of 1,1-dichloro-2-benzoyloxy-4-methyl-3-pentene by-product can be isolated from the distillation residue.

EXAMPLE 10

The procedure described in Example 1 is followed except that instead of pure 1,1,1-trichloro-2-acetoxy-4-methyl-3-pentene 1,1,1-trichloro-2-acetoxy-4-methyl-3-pentene containing 10% of isomeric 1,1,1-trichloro-2-acetoxy-4-methyl-4-pentene is employed. 25.8 g. (84%) of distilled 1,1-dichloro-4-methyl-1,3-pentadiene are obtained. The analytical characteristics of the product are identical with the product of Example 1. From the residue 8.1% of a by-product can be isolated.

EXAMPLE 11

The procedure described in Example 1 is followed except that the reaction is carried out at 0° C. 27.9 g. (91%) of 1,1-dichloro-4-methyl-1,3-pentadiene are obtained.

EXAMPLE 12

50.0 g. (0.246 moles) of 1,1,1-trichloro-2-hydroxy-4-methyl-4-pentene are admixed with 30.1 g. (0.295 moles) of acetic anhydride, whereupon 3 drops of a concentrated sulfuric acid solution are added to the mixture, which is then stirred for 10 minutes. 1,1,1-trichloro-2-acetoxy-4-methyl-4-pentene is obtained in the reaction which can be detected by t.l.c. measurement (Merck Art. No. 5715 analytical sheet, benzene; R_f for the starting material: 0.34, R_f for the acetylated product: 0.66). The reaction mixture obtained and 123 ml. of a 2 N aqueous sodium hydrogensulfate solution are simultaneously added to a suspension of 32.2 g. (0.492 moles) of zinc powder in 200 ml. of methanol in 10 minutes, under vigorous stirring, while keeping the reaction vessel on a water bath of 10°–15° C. When the addition is complete, the mixture is stirred for another 5 minutes, whereupon the solids are filtered off.

The substance remaining on the filter is washed with 50 ml. of methanol and three 50-ml. portions of dichloromethane. The filtrates are combined and to the mixture 800 ml. of water are added. The phases are shaken in a separating funnel, the organic phase is separated and the aqueous phase is extracted with three 30-ml. portions of methylene chloride. The organic phases are combined, dried over sodium sulfate, filtered and the organic solvents are distilled off, using a 50-cm. Vigreaux column. The residue is fractioned under a pressure of 10 to 15 mmHg. The product is obtained in the fraction distilling off at 40° to 60° C. 33.0 g. (89%) of 1,1-dichloro-4-methyl-1,4-pentadiene are obtained. The physical characteristics of the product are identical with those of the product obtained in Example 4.

EXAMPLE 13

50 g. (0.246 moles) of 1,1,1-trichloro-2-hydroxy-4-methyl-4-pentene are admixed with 30.1 g. (0.295 moles) of acetic anhydride. To the mixture 2.5 g. (0.025 moles) of concentrated sulfuric acid are added in 10 minutes and the mixture is stirred for 10 minutes. 1,1,1-trichloro-2-acetoxy-4-methyl-4-pentene is obtained as shown by thin layer chromatography (Merck Art. No. 5715, benzene, R_f for starting compound: 0.4 and R_f for the acetylated product: 0.63).

The reaction mixture obtained is added to a suspension of 32.2 g. (0.492 moles) of zinc powder in 200 ml. of methanol in 10 minutes, under vigorous stirring, while keeping the flask in a water bath of 10° to 15° C. After the addition the mixture is stirred for 5 additional minutes, whereupon the solids are filtered off. The solid substance on the filter is washed with three 10-ml. portions of dichloromethane. The filtrates are combined and 400 ml. of water are added to the mixture. The phases are separated in a separating funnel and the aqueous phase is extracted with two 30-ml. portions of carbon tetrachloride.

The combined organic phases are dried over sodium sulfate, filtered and the organic solvent are distilled off using a 25-cm. Vigreux column. The residue is fractioned under a pressure of 15 to 20 mmHg.

33.0 g. (80%) of 1,1-dichloro-4-methyl-1,4-pentadiene are obtained. The physico-chemical characteristics of the product are identical with those of the product of Example 4.

We claim:

1. A process for the preparation of a compound of the formula (I)

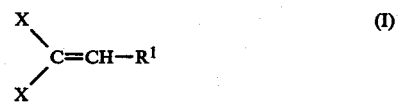

wherein
X is halogen,
R¹ is a straight or branched chain alkenyl group having 2 to 6 carbon atoms, which comprises reacting a compound of the formula (II)

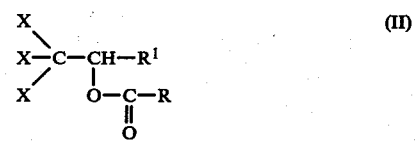

wherein
X and R' have the same meaning as defined above, and
R is hydrogen, a straight or branched chain alkyl group having 1 to 6 carbon atoms or an optionally substituted aryl or aralkyl group, with 1 to 2 mol.-equivalents of zinc, aluminum, tin, iron or magnesium and 0.01 to 1.5 mol.-equivalents of a mineral acid and/or acidic salt thereof, in a watermiscible organic solvent, at a temperature between 0° C. and 200° C.

2. A process as defined in claim 1, which comprises adding a solution of a compound of the formula (II) in a water-miscible organic solvent and an aqueous solution of a mineral acid simultaneously to a suspension of 1 to 2 mol.-equivalents of zinc, aluminum, tin, iron or magnesium powder in an organic solvent.

3. A process as defined in claim 1, which comprises adding a solution of a compounds of the formula (II) and 0.01 to 0.1 mol.-equivalents of a mineral acid and/or an acidic salt thereof in a water-miscible organic solvent to a suspension of 1 to 2 mol.-equivalents of zinc, aluminum, iron or magnesium powder in a water-miscible organic solvent.

4. A process as defined in claim 1, which comprises using as a water-miscible organic solvent alkanols having 1 to 4 carbon atoms, tetrahydrofuran or dimethoxyethane; oxo-compounds, acetone; carboxylic acids having 1 to 4 carbon atoms, or carboxylic acid anhydrides having 3 to 6 carbon atoms.

5. A process as defined in claim 1, which comprises carrying out the reaction at the boiling temperature of the mixture of an organic solvent and water.

6. A process as defined in claim 1, which comprises using as a mineral acid hydrochloric acid, sulfuric acid, phosphoric acid or perchloric acid.

7. A process as defined in claim 1, which comprises using as an acid salt an alkali hydrosulfate, alkali hydrogenphosphate or alkali dihydrogenphosphate.